(12) United States Patent
Zhao et al.

(10) Patent No.: US 7,822,484 B1
(45) Date of Patent: Oct. 26, 2010

(54) MRI-COMPATIBLE IMPLANTABLE LEAD HAVING HIGH IMPEDANCE ELECTRODES

(75) Inventors: Yong D. Zhao, Simi Valley, CA (US); Virote Indravudh, Santa Clarita, CA (US); Xiaoyi Min, Thousand Oaks, CA (US); Geoff Daush, Santa Clarita, CA (US)

(73) Assignee: Pacesetter, Inc., Sylmar, CA (US)

( * ) Notice: Subject to any disclaimer, the term of this patent is extended or adjusted under 35 U.S.C. 154(b) by 288 days.

(21) Appl. No.: 11/696,020

(22) Filed: Apr. 3, 2007

(51) Int. Cl.
*A61N 1/05* (2006.01)
(52) U.S. Cl. .................. 607/116; 607/127; 600/375
(58) Field of Classification Search ............... 607/116, 607/119, 122–123, 126–128, 131; 600/375
See application file for complete search history.

(56) References Cited

U.S. PATENT DOCUMENTS

| | | | | |
|---|---|---|---|---|
| 4,662,382 A * | 5/1987 | Sluetz et al. | ............... | 607/126 |
| 5,003,992 A * | 4/1991 | Holleman et al. | ........... | 607/120 |
| 5,076,285 A * | 12/1991 | Hess et al. | ................... | 607/127 |
| 5,447,533 A * | 9/1995 | Vachon et al. | ............... | 607/120 |
| 6,345,204 B1 * | 2/2002 | Scheiner et al. | ............. | 607/123 |
| 2003/0144719 A1 * | 7/2003 | Zeijlemaker | ................ | 607/122 |
| 2005/0049665 A1 * | 3/2005 | Brabec et al. | ................ | 607/122 |

* cited by examiner

*Primary Examiner*—Mark W Bockelman
*Assistant Examiner*—Erica Lee

(57) ABSTRACT

An implantable lead includes a lead body, having a distal end and a proximal end, configured to be implanted in a patient. An electrode assembly is provided at the distal end of the lead body, wherein the electrode assembly includes an electrode that is configured to deliver stimulating pulses. The electrode extends between a base and a tip at a distal end of the electrode. A shielding member is provided on the electrode assembly and is positioned to cover at least a portion of the electrode to electrically shield the electrode from RF fields. Optionally, the shielding member may include a shielding conductor that wraps about and extends longitudinally along a length of the electrode from the base to the tip. The shielding conductor may extend from the proximal end of the lead body at least to the distal end of the lead body.

16 Claims, 3 Drawing Sheets

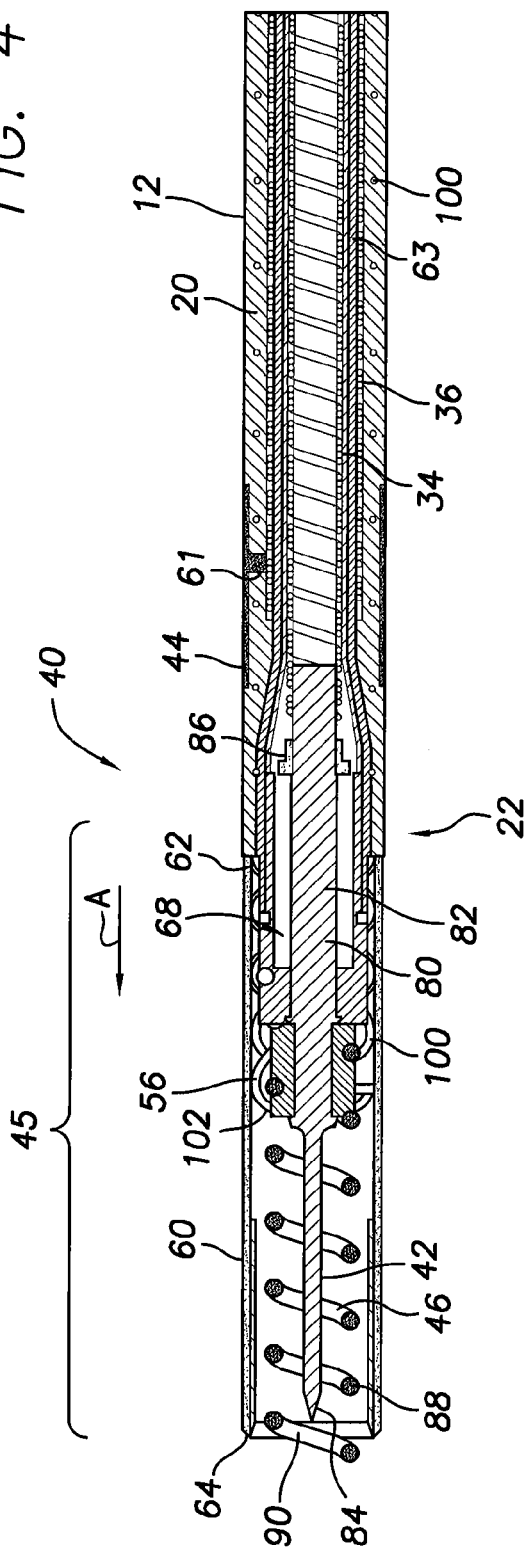

MRI-COMPATIBLE IMPLANTABLE LEAD HAVING HIGH IMPEDANCE ELECTRODES

BACKGROUND OF THE INVENTION

The various embodiments described herein generally relate to implantable leads, and more particularly to MRI-safe implantable leads having high impedance electrodes.

An implantable medical device is implanted in a patient to, among other things, monitor electrical activity of a heart and to deliver appropriate electrical and/or drug therapy, as required. Implantable medical devices ("IMDs") include for example, pacemakers, cardioverters, defibrillators, implantable cardioverter defibrillators ("ICD"), and the like. The electrical therapy produced by an IMD may include, for example, pacing pulses, cardioverting pulses, and/or defibrillator pulses to reverse arrhythmias (e.g. tachycardias and bradycardias) or to stimulate the contraction of cardiac tissue (e.g. cardiac pacing) to return the heart to its normal sinus rhythm.

In general, the IMD includes a battery and electronic circuitry, such as a pulse generator and/or a processor module, that are hermetically sealed within a housing (generally referred to as the "can"). An implantable lead interconnects the IMD and the heart. The lead generally includes a pacing electrode and at least one sensing electrode at a tip of the lead. Electrical signals are transmitted between the electrodes and the pulse generator. For an IMD, functional implant life time is, in part, determined by the energy delivered per pulse. The IMD will have a longer life if the energy delivered per pulse can be maintained at a minimum. Designs of the lead and of the electrodes which are used with the lead are influenced by the electrical signal required for pacing stimulation. Physiologically, the IMD should be capable of generating a signal with a sufficient magnitude to depolarize the excitable cells of the myocardium to initiate contraction. The electrode shape, size, surface area, material and impedance combine to determine the energy required of the IMD.

When patients implanted with IMD's are subjected to external electromagnetic interference, undesirable electric current and voltage could be induced by such interference and could create undesirable physiological effects, such as fibrillation and pain. Examples of IMD malfunctions have been traced to medical procedures, such as radiofrequency catheter ablation, electrocautary, dental procedures, magnetic resonance imaging (MRI) techniques, as well as other medical procedures. Of these, the MRI system is perhaps the most common.

MRI is a technique that provides a non-invasive method for the examination of the internal anatomy of a human body. This provides an efficient means for diagnosing disorders such as neurological and cardiac abnormalities. However, it may be unsafe and even hazardous to place patients implanted with IMD's through the MRI system because of the high radiofrequency (RF) field that is generated. The high RF field may cause heating of the conductive components of the IMD, such as the housing, the lead, and the electrodes. The heat energy then dissipates to the surrounding tissues, thereby causing damage. Further, the high RF field may cause a high current to flow through the leads and within internal components of the IMD. As a result, the MRI system may cause the IMD to generate a voltage at the leads that then electrically excites the tissue. In certain instances, the voltage generated at the leads may induce fibrillation of the heart. The current induced by the RF field of the MRI system may also inhibit the output of pacing pulses to the patient.

Methods have been proposed to reduce the effects of interference by MRI systems on implantable medical devices. Some of these methods focus on reducing the effects of interference on the lead itself. Certain conventional leads have increased insulation surrounding the lead body, or have wires or conductors within the lead with reduced diameter to limit the effects of the RF fields. However, adding insulation or reducing the size of wires or conductors may increase the cost of the lead and may decrease the effectiveness of the IMD. Other known leads include a shield, such as a conductor or a wire braid, within portions of an insulating sheath surrounding the lead. However, conventional shield arrangements are unable to shield the pacing and/or sensing electrodes at the end of the lead. The electrodes remain unshielded, and thus are subject to excessive heating and the like.

A need remains for an improved, MRI-compatible, implantable lead that may be safely used during imaging with MRI systems without the generation of significant heat beyond safe temperature levels.

SUMMARY

In accordance with one embodiment, an implantable lead is provided including a lead body, having a distal end and a proximal end, configured to be implanted in a patient. An electrode assembly is provided at the distal end of the lead body, wherein the electrode assembly includes an electrode that is configured to deliver stimulating pulses. The electrode extends between a base and a tip at a distal end of the electrode. A shielding member is provided on the electrode assembly and is positioned to cover at least a portion of the electrode to electrically shield the electrode from RF fields.

Optionally, the shielding member may include a shielding conductor that wraps about and extends longitudinally along a length of the electrode from the base to the tip. The shielding conductor may be conically shaped and may be arranged concentrically about the electrode. The shielding conductor may be helically wound about the electrode. The shielding conductor may extend from the proximal end of the lead body at least to the distal end of the lead body. Optionally, the electrode assembly may include a shaft member advanceable with respect to the distal end of the lead body, wherein the electrode is coupled to the shaft member and is advanceable therewith, and the shielding conductor is coupled to the shaft member and is advanceable therewith.

In accordance with another embodiment, an implantable lead is provided including a lead body, having a distal end and a proximal end, configured to be implanted in a patient. A stimulating electrode assembly is provided at the distal end of the lead body, wherein the stimulating electrode assembly includes a housing that holds an electrode therein that is configured to deliver stimulation pulses. The electrode has a conductive body extending between a base and a tip. A fixation helix is received within the housing for securing the electrode to the cardiac tissue of the patient. The fixation helix wraps about at least a portion of the electrode. A shielding conductor is electrically coupled to the fixation helix, wherein the shielding conductor and the fixation helix cooperate to electrically shield at least a portion of the electrode from RF fields.

In accordance with a further embodiment, an implantable lead is provided including a lead body, having a distal end and a proximal end, configured to be implanted in a patient and a pacing conductor extending between the distal end and the proximal end. An electrode assembly is provided at the distal end of the lead body, wherein the electrode assembly includes a housing that holds a fixation helix and an electrode. The electrode is electrically coupled to the pacing conductor and is configured to deliver stimulation pulses. A shielding member is provided within the lead body and surrounds at least a portion of the pacing conductor to electrically shield the pacing conductor.

BRIEF DESCRIPTION OF THE DRAWINGS

FIG. 4 illustrates a partial cross-section of an electrode assembly of the pacing lead shown in FIG. 2 showing the electrode assembly in a retracted state.

FIG. 5 illustrates the electrode assembly shown in FIG. 4 in an extended state.

DETAILED DESCRIPTION

Figure 1:
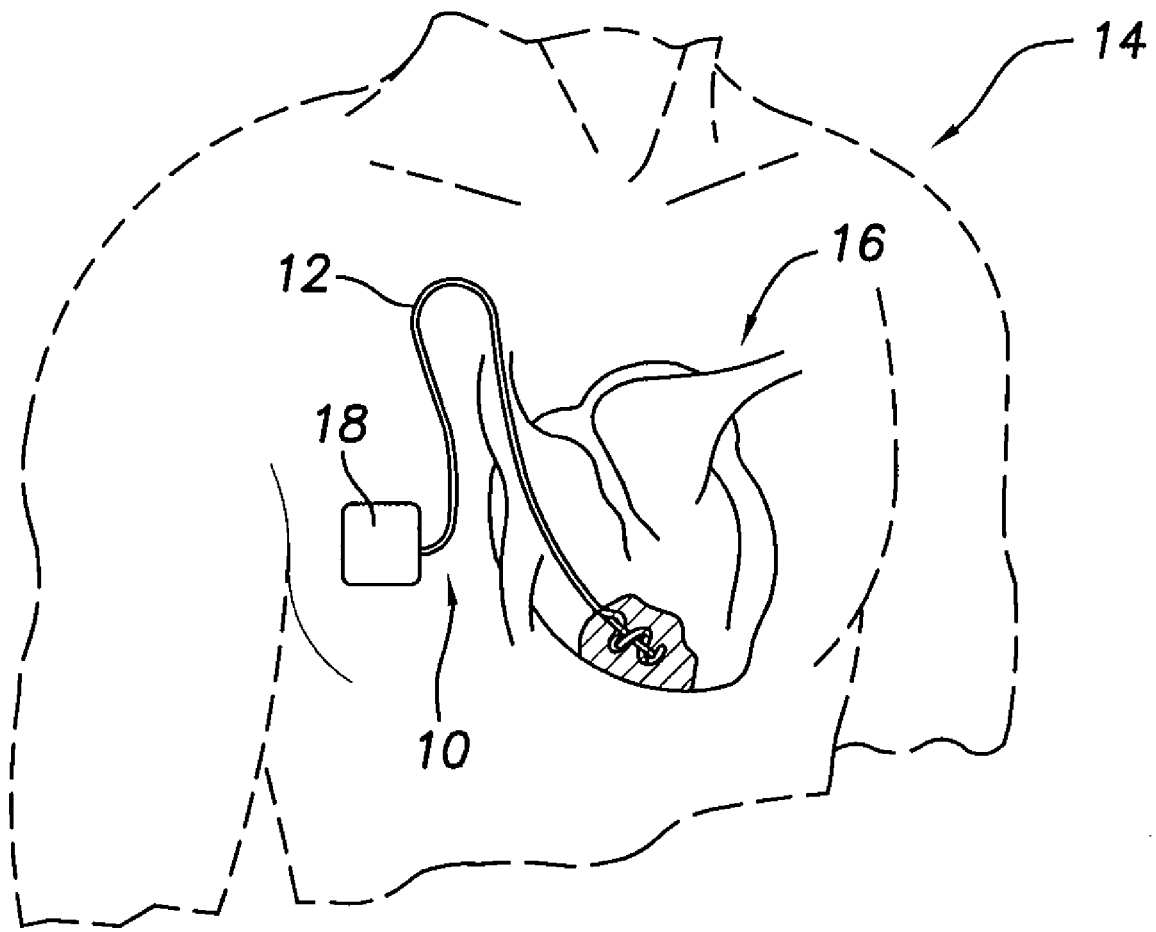
FIG. 1 illustrates an implanted medical system including a pacing lead formed in accordance with an exemplary embodiment.

FIG. 1 illustrates an implantable medical system 10 including an implantable lead 12 formed in accordance with an exemplary embodiment. FIG. 1 depicts a chest cavity 14 in phantom, and a heart 16 within the chest cavity 14. The medical system 10 includes an implantable medical device 18, such as a pacemaker, and the lead 12, which are both implanted in the chest cavity 14. Optionally, the medical device 18 may be implanted elsewhere, such as in the patient's abdomen. In the illustrated embodiment, the lead 12 is a bipolar pacing and sensing lead, however other types of leads may be used in alternative embodiments. Although the following embodiments are described principally in the context of pacemaker/defibrillator unit capable of sensing and/or pacing pulse delivery, the medical system 10 may be applied to other IMD structures. As further examples, embodiments may be implemented in devices that suppress an individual's appetite, stimulate the patients nervous or muscular systems, stimulate the patient's brain functions, reduce or offset pain associated with chronic conditions and control motor skills for handicap individuals, and the like.

Figure 2:
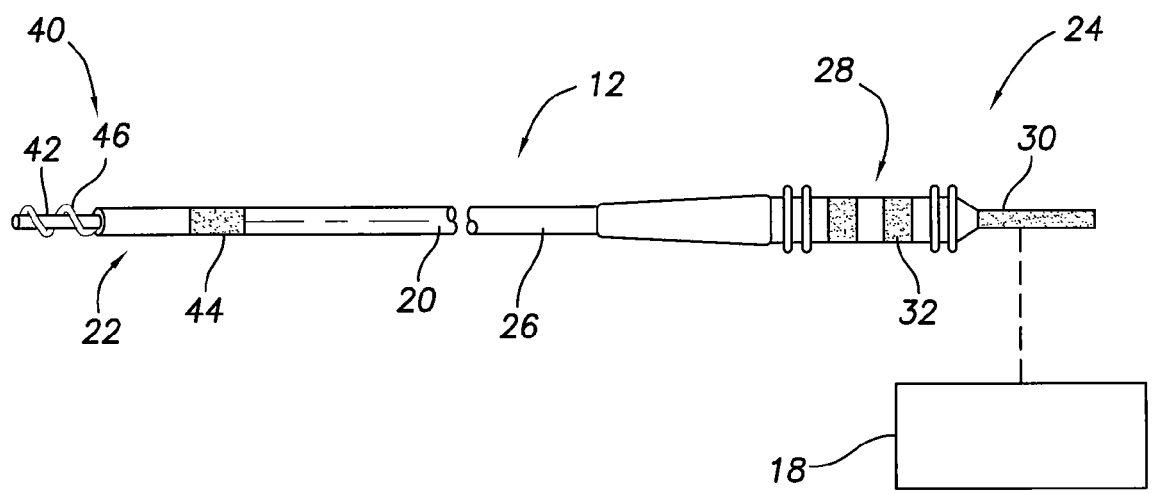
FIG. 2 illustrates the pacing lead shown in FIG. 1.

FIG. 2 illustrates the lead 12 as having an elongated lead body 20 which includes a distal end portion 22 and a proximal end portion 24. The lead body 20 has a length that extends along a longitudinal axis between the distal and proximal end portions 22 and 24. The term longitudinal axis encompasses both linear and non-linear axes. The longitudinal axis of the lead body 20 extends along a curved path that changes as the lead body 20 is flexed, bent and otherwise manipulated. The lead body 20 includes an insulating sheath 26 of a suitable insulative, biocompatible, biostable material such as, for example, PEEK (i.e. Polyetheretherketones), silicone rubber or polyurethane, extending substantially the entire length of the lead body 20.

A connector assembly 28 is provided at the proximal end portion 24 of the lead 12. The connector assembly 28 is configured to be inserted into a receiving orifice in the implantable medical device 18 (shown in FIG. 1). The connector assembly 28 includes first and second electrical terminals 30, 32 each being connected to respective electrical conductors, such as pacing and sensing electrical conductors 34, 36 illustrated in FIGS. 3-5. The pacing and sensing electrical conductors 34, 36 are surrounded by the insulating sheath 26. While the following embodiments are described principally in the context of pacing and sensing electrical conductors, the conductors are not intended to be limited to pacing and sensing conductors. For example, only pacing or only sensing conductors may be used. Alternatively, other types of lead conductors may be used that are not used for pacing or sensing.

An electrode assembly 40 is provided at the distal end portion 22 of the lead 12. The electrode assembly 40 includes a tip electrode 42 at the distal end portion 22 and a ring electrode 44 proximate to the distal end portion 22. The tip electrode 42 is electrically connected to the first electrical terminal 30 by the electrical conductor 34. Similarly, the ring electrode 44 is connected to the second electrical terminal 32 by the electrical conductor 36. In an alternative embodiment, the electrode assembly 40 may include only the tip electrode 42 without a corresponding ring electrode.

The lead 12 includes, at the distal end portion 22, a fixation mechanism 46 that functions to interlock the lead 12 within the cardiac tissue at the implantation site and thereby prevent inadvertent displacement of the distal end portion 22 once the lead 12 is implanted. In the illustrated embodiment, the fixation mechanism 46 is represented by a screw-in helix that penetrates the cardiac tissue to anchor the lead 12 thereto. While the helix represents one type of fixation mechanism 46, optionally other fixation mechanisms may be utilized and the fixation mechanisms may include any suitable structures, elements, components, configurations, arrangements, and/or geometries that securely position and hold the distal end portion 22 in the positions (e.g., location and/or orientation) described and/or illustrated herein.

Figure 3:
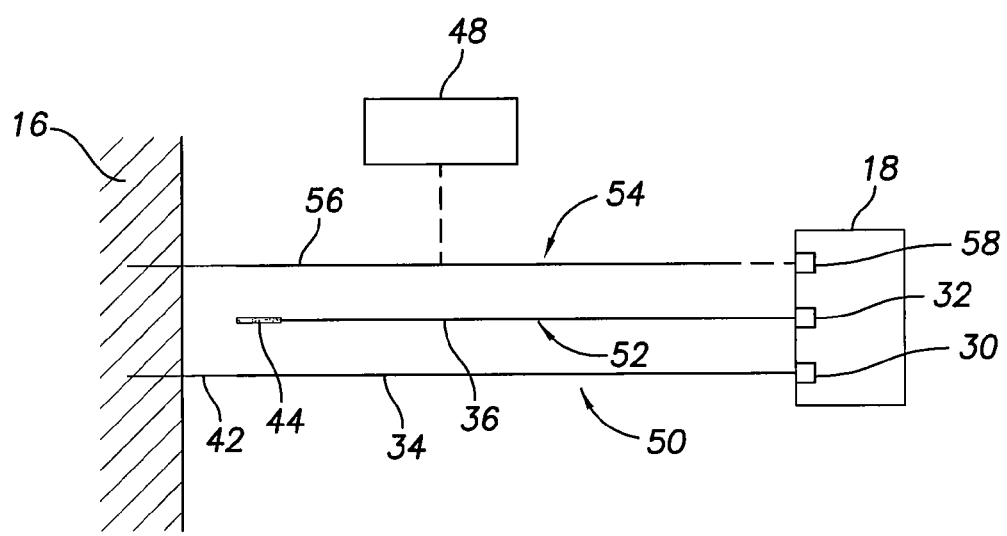
FIG. 3 schematically illustrates pacing, sensing and shielding circuits for the pacing lead shown in FIG. 2.

FIG. 3 schematically illustrates an MRI system 48 positioned with respect to a pacing circuit 50, a sensing circuit 52, and a shielding member 54 for the lead 12 (shown in FIG. 2). Each of the circuits 50, 52 and the shielding member 54 are provided within, and extend along, the lead body 20 (shown in FIG. 2). The shielding member 54 is electrically insulated from the pacing and sensing circuits 50 and 52, and be used to shield the pacing and sensing circuits 50, 52 from electromagnetic fields and/or radiofrequency signals emitted from the MRI system 48. The electromagnetic fields and/or radiofrequency signals are generally illustrated by the dashed line emitted from the MRI system 48 in FIG. 3.

The pacing circuit 50 includes the pacing conductor 34 and the tip electrode 42, which defines, and is sometimes referred to hereinafter as, a pacing electrode 42 or a stimulating electrode 42. The tip electrode 42 is implanted within the patient's tissue that is to be treated or stimulated, such as the heart 16. The pacing conductor 34 is terminated to the medical device 18 at the first electrical terminal 30. The pacing conductor 34 transmits signals between the medical device 18 and the tip electrode 42. In an alternative embodiment, the pacing circuit 50 may include at least one inductor (not shown) coupled proximate to the distal end of the pacing conductor 34.

The sensing circuit 52 includes the second conductor 36 and the ring electrode 44, which defines, and is sometimes referred to hereinafter as, a sensing electrode 44. The sensing conductor 36 is terminated to the medical device 18 at the second electrical terminal 32. The sensing conductor 36 transmits signals between the medical device 18 and the ring electrode 44.

The shielding member 54 includes a shielding conductor 56 that extends at least partially along the length of the lead 12 between the distal end portion 22 (shown in FIG. 2) and the proximal end portion 24 (shown in FIG. 2). Optionally, the shielding conductor 56 may extend all the way to, or even beyond, the distal end portion 22. The shielding conductor 56 may also extend all the way to the proximal end portion 24. In an exemplary embodiment, the shielding conductor 56 includes the fixation mechanism 46 as part of the shielding member 54. The fixation mechanism 46 shields at least a portion of the tip electrode 42, such that the shielding member 54 shields the pacing component of the pacing circuit 50. The shielding conductor 56 may be terminated to the medical device 18, such as at a third electrical terminal 58. However, in alternative embodiments, the shielding conductor 56 may not engage, or otherwise terminate to, the medical device 18. In an alternative embodiment, the shielding member 54 may include at least one resistor coupled to the shielding conductor 56. In another alternative embodiment, the shielding member 54 may include, or may be coupled to, a ground conductor (not shown) extending along a length of the lead 12 and that is connected to the medical device 18.

The shielding conductor 56 may include one or more wires or other conductive elements that cover, or otherwise electrically shield, at least a portion of the pacing circuit 50 and at least a portion of the sensing circuit 52. For example, the shielding conductor 56 may be a wire or a plurality of wires helically wound about the lead 12 along the length of the lead 12. Alternatively, the shielding conductor 56 may be a wire mesh, a solid conductive tube, shielding strips, a metalized fabric layer, a conductive gasket, or the like, that extends along the length of the lead 12. In other alternative embodiments, the shielding conductor 56 may be a conductive elastomer or a conductive foam extending along the lead body 20. Optionally, the shielding conductor 56 may be embedded within the lead body 20, may extend along either an inner or outer surface of the lead body, or may extend along channels formed within the lead body 20. In another alternative embodiment, the shielding conductor 56 may be an embedded layer of particles within the lead body 20 electrically isolated from, and operating to shield, the pacing and sensing circuits 50, 52.

FIG. 4 illustrates a partial cross-section of the electrode assembly 40 of the pacing lead 12 while the electrode assembly 40 is in a retracted state. FIG. 5 illustrates the electrode assembly 40 in an extended state, and will be discussed in further detail below. The fixation mechanism 46 and the tip electrode 42 of the electrode assembly 40 are advanceable in the direction of arrow A to an extended position to penetrate, and become fixed to, the myocardium of the heart 16 (shown in FIG. 1) upon implantation. In the retracted state, the fixation mechanism 46 and the tip electrode 42 are enclosed to facilitate implantation to a desired location, and are extended once the distal end portion 22 is properly positioned proximate the myocardium of the heart 16. When retracted, an outer end or tip 90 of the fixation mechanism 46 and an outer end or tip 84 of the tip electrode 42 are positioned within the outer lumen section 45, and are drawn inward from or flush with the tissue engaging end 64 of the housing 60. Alternatively, one or both of the tip 84 and the tip 90 may slightly project from the outer lumen section 45 beyond the tissue engaging end 64 of the housing 60.

In an alternative embodiment, the fixation mechanism 46 and/or the tip electrode 42 are fixed in relation to the end of the lead 12 rather than being advanceable. In such embodiment, the fixation mechanism 46 and/or the tip electrode 42 are exposed, and extend beyond, the end of the lead 12 to engage the tissue of the heart 16 during implantation.

The electrode assembly 40 generally includes the various electrodes and sensors used by the implanted medical system 10 (shown in FIG. 1) for monitoring and/or pacing the heart 16 (shown in FIG. 1). The electrode assembly 40 includes the tip and ring electrodes 42, 44 and receives the pacing, sensing and shielding conductors 34, 36, 56. Alternatively, the electrode assembly 40 may include more than one ring electrode or the electrode assembly 40 may not include any ring electrodes. The tip electrode 42 operates as a pacing electrode and the ring electrode 44 operates as a sensing electrode. A pacing electrode is configured to provide pacing signals to the tissue of the heart for electrically stimulating the heart tissue by delivering an electrical charge to the heart tissue. A pacing electrode consumes power from the battery of the implantable medical device 18 (shown on FIG. 1) and when battery life is a design consideration, consideration is given to the characteristics of the pacing electrode, such as the size, shape, material, surface area, and impedance of the pacing electrode. Optionally, a pacing electrode may also operate as a sensing electrode. A sensing electrode is not configured for stimulating the tissue of the heart, but rather is used to detect electrical activity of the heart. Because the use of a sensing electrode does not affect the battery life of the implantable medical device 18 in a noticeable amount, battery life is not typically a design consideration of a sensing electrode.

As illustrated in FIG. 4, the tip electrode 42 is coupled to the pacing conductor 34, such as by a crimp connection, a friction fit connection, a soldered connection, using a conductive adhesive, and the like. The ring electrode 44 is coupled to the sensing conductor 36, such as by using an interconnect 61 between the components. Alternatively, the ring electrode may directly engage the sensing conductor 36 and may be securely coupled thereto. The pacing and sensing conductors 34, 36 are separated from one another by an insulating layer 63.

The electrode assembly 40 includes a housing 60 attached to the distal end portion 22 of the lead 12. The housing 60 is a hollow, tubular element extending between a lead mating end 62 and a tissue engaging end 64. The lead mating end 62 of the housing 60 is mechanically secured to the distal end portion 22 of the lead 12, such as by a friction fit, however, other attachment means may be used, such as adhesive, soldering, and the like. In the illustrated embodiment, the insulating layer 63 of the lead 12 is captured between the housing 60 and a tubular insert 66 to secure the housing 60 to the distal end portion 22 of the lead 12. The tubular insert 66 includes an inner chamber 68 extending between opposed ends. Optionally, a portion of the insert 66 is located within the housing 60 and another portion of the insert 66 is located within the lead body 20.

In an exemplary embodiment, the housing 60 is electrically inactive such that no portion of the housing 60 interacts electrically with the cardiac tissue of the patient. Optionally, the housing 60 may be fabricated from a suitable insulative, biocompatible, biostable material. Alternatively, the housing 60 may be fabricated from a biocompatible, biostable metal or metal alloy having an insulative coating surrounding at least all portions of the housing 60 that may engage the cardiac tissue of the patient. Optionally, the housing 60 may include at least one fluoro-marker (not shown), or other suitable means, for identifying a position of the distal end portion 22 during and/or after implantation within the patient.

As described above, the tip electrode 42 is movably received within the housing 60. Optionally, at least a portion of the tip electrode 42 may also be movably received within the distal end portion 22 of the lead body 20. In an exemplary embodiment, the tip electrode 42 is represented by, and sometimes referred to hereinafter as, a pin electrode 42. The pin electrode 42 includes an elongated shaft or body 80 extending between a base 82 and a tip 84. In an exemplary embodiment, the elongated body 80 is non-hollow, or solid, and is fabricated from a biocompatible, biostable conductive material, such as a metal, a metal alloy, a conductive polymer, and the like. However, the elongated body 80 may be hollow in alternative embodiments. Optionally, at least a portion of the pin electrode 42, such as a portion proximate the tip 84, may be coated with a porous coating, such as a titanium nitride or platinum black coating, for electrical performance enhancement. The base 82 is directly connected to the pacing conductor 34 for receiving pacing signals therefrom. By directly connecting the pin electrode 42 to the pacing conductor 34, a reliable interconnection may be provided. Alternatively, interconnects, or other conductive elements, may be used to provide the electrical connection between the pin electrode 42 and the pacing conductor 34.

In an exemplary embodiment, the pin electrode 42 is rotatably mounted within the inner chamber 68 of the insert 66. A guide member 86 may be provided at the base 82 of the pin electrode 42 to position the pin electrode 42 within the insert 66 as the pin electrode 42 is advanced to the extended position (shown in FIG. 5). For example, a stylet with a driving head (not shown) or other advancing mechanism may be used to rotate, or otherwise force, the pin electrode 42 to the extended position. The guide member 86 is provided to maintain the axial position of the pin electrode 42 relative to the insert 66 and the housing 60. Additionally, at least a portion of the insert 66 may be dimensioned substantially similar to the pin electrode 42 such that the walls of the insert 66 support and position the pin electrode 42. Optionally, a seal (not shown) may be provided between the pin electrode 42 and the insert 66 to seal against the inflow of bodily fluid during or after implantation.

As described above, the fixation mechanism 46 is illustrated in the Figures, and is sometimes referred to hereinafter, as a screw-in helix 46 or helix 46. The helix 46 includes a cylindrical body 88 that is wound about a longitudinal axis that coincides with the longitudinal axis of the lead 12. A tip 90 is provided at the distal end of the helix 46. The helix 46 is axially centered within the housing 60 and the longitudinal axis of the helix 46 is coincident with the pin electrode 42 such that the pin electrode 42 is centered within the helix 46 and within the housing 60. Optionally, the helix 46 may be fabricated from a conductive material, but include an insulative, biocompatible, biostable coating surrounding at least a portion of the helix 46 such that the helix 46 is electrically inactive, wherein no portion of the helix 46 interacts electrically with the cardiac tissue of the patient. Alternatively, the helix 46 may be fabricated from a non-conductive, biocompatible, biostable material such as, for example, PEEK, polyurethane or hardened rubber.

In the exemplary embodiment, the helix 46 is movable with respect to the housing 60 between the retracted position and the extended position. Similar to the pin electrode 42, a stylet (not shown) or other advancing mechanism may be used to rotate, or otherwise force, the helix 46 to the extended position. In an exemplary embodiment, a shaft ring 92 is secured to the pin electrode 42, such as by an adhesive, an epoxy, welding, crimping and the like. The helix 46 is then secured to the shaft ring 92, such as by welding or crimping. Optionally, the shaft ring 92 may be coated with an insulation or fabricated from a non-conductive material such that the helix 46 is electrically isolated from the pin electrode 42. The shaft ring 92 allows the pin electrode 42 and the helix 46 to be advanced simultaneously. For example, as the pin electrode 42 is rotated, the helix 46 is similarly rotated. Alternatively, the shaft ring 92 may be movable with respect to the helix 46. For example, the shaft ring 92 and/or the housing 60 may include grooves that transfer lateral movement of the shaft ring 92 to rotational movement of the helix 46.

The shielding conductor 56 extends along the lead 12 to the distal end portion 22 of the lead 12. In an exemplary embodiment, the shielding conductor 56 includes a wire 100 extending for a length along the longitudinal axis of the lead 12. In an exemplary embodiment, the helix 46 defines a portion of the shielding conductor 56, as will be explained in detail below. The wire 100 may be fabricated from a material suited for shielding against electromagnetic fields and/or radiofrequency signals, such as non-ferrous metals and/or non-magnetic metals, and the density of the material may be selected depending on the particular application and the particular frequency spectrum. The wire 100 of the shielding conductor 56 may be embedded within the insulating sheath 26 such that the wire 100 is insulated from the pacing and sensing conductors 34, 36 and from the exterior environment of the lead 12. The wire 100 is positioned radially outward of the pacing and sensing conductors 34, 36 to shield those conductors 34, 36 from electromagnetic fields and/or radiofrequency signals. The wire may have any cross-sectional shape, such as round, square, rectangular, and the like. The wire 100 extends beyond the distal end portion 22 into the housing 60. Optionally, multiple wires 100 may be provided and braided or woven into a wire braid extending along the lead 12. The wire braid may have any number of braid profiles depending on the particular application. In the illustrated embodiment, the individual wires 100 in the braid are flexible and are helically wound around an outer portion of the lead 12. The wires 100 thus circumferentially surround and cover the pacing and sensing conductors 34, 36. Alternatively, the wires 100 may extend generally linearly along the lead 12 rather than helically. In an alternative embodiment, rather than the wires 100, the shielding conductor 56 may include a foil or conductive powder extending the length of the lead 12.

The wires 100 extend from the insulating sheath 26 into the housing 60. The wires 100 are positioned between an inner surface of the housing 60 and an outer surface of the insert 66. The wires 100 extend to a tip 102 at a distal end of the wires 100. Optionally, the tip 102 may be aligned with the pin electrode 42 such that the wires 100 concentrically cover at least a portion of the pin electrode 42. As such, the pin electrode 42 is directly shielded by the shielding conductor 56 and the shielding member 54. In an exemplary embodiment, the wires 100 shield at least a majority of the pin electrode 42. In the illustrated embodiment, the wires 100 are terminated to the shaft ring 92 such as by using an adhesive, crimping, soldering, welding, or the like. The wires 100 are movable with the shaft ring 92 between a retracted position (shown in FIG. 4) and an extended position (shown in FIG. 5). Optionally, the flexibility of the wires 100 allow the wires 100 to be stressed in tension, compression, bending and/or torsion as the lead 12 is manipulated and/or as the wires 100 are moved between the extended and retracted positions.

As described above, the wires 100 and the helix 46 may cooperate to define the shielding conductor 56. For example, during assembly, the wires 100 are directly coupled to the helix 46 at the shaft ring 92 by coupling the wires 100 to the helix 46 or by coupling the helix 46 to the wires 100. While the helix 46 may be insulated using a coating, a portion of the helix 46 may be uncoated to electrically connect to the wires 100 and create a shielding circuit along the shielding member 54. Rather than terminating the wires 100 to the helix 46, the helix 46 may be hollow and the wires 100 may extend through the hollow portion of the helix 46 to a point at or near the tip 90 of the helix 46. As such, the wires 100 may extend to completely cover the tip electrode 42. Optionally, the helix 46 and the wires 100 may be unitarily formed into a one piece body having a fixation portion at the distal end thereof for attaching to the patient. The fixation portion may be stiffened such that the fixation portion is rigid and the fixation portion may be coated to electrically isolate the fixation portion from the patient. In an alternative embodiment, rather than direct coupling, the wires 100 may be indirectly coupled to the helix 46 by coupling both the wires 100 and the helix 46 to the shaft ring 92, and electrically interconnecting the wires 100 and the helix 46, such as by using a conductive interconnect therebetween, or by providing at least a partially conductive shaft ring 92. In another alternative embodiment, the wires 100 and the helix 46 may not be electrically coupled to one another, but rather, the helix 46 may be electrically isolated from the wires 100.

FIG. 5 illustrates the helix 46 and the pin electrode 42 of the electrode assembly 40 in the extended state. In the extended state, the helix 46 and the pin electrode 42 protrude beyond the tissue engaging end 64 of the housing 60. As such, the helix 46 and the pin electrode 42 are capable of physically penetrating the heart tissue. As such, during pacing, the pin electrode 42 is capable of directly transmitting the pacing signals to inner layers of the heart tissue that are beyond the surface of the heart. Physically penetrating the heart tissues may increase the effectiveness of the pacing and may reduce the amount of energy needed to effectively pace the heart tissue.

As described above, because the wires 100 are fixed with respect to the helix 46 and pin electrode 42, the wires 100 are also moved to an extended position. The wires 100 thus provide shielding to the pin electrode 42 when the pin electrode 42 is in the extended state. Additionally, because the relative position of the pin electrode 42 and the shielding conductor 56 (e.g. the wires 100 and the helix 46) remains the same as the electrode assembly 40 is advanced to the extended state, the pin electrode 42 remains shielded in both the extended and retracted states. As the electrode assembly 40 is moved to the extended state, the wires 100 are wound and stretched outward toward the tissue engaging end 64. The wires 100 are flexible to allow for movement of the wires 100 between the retracted and extended positions.

As described above, an advancing mechanism (not shown), such as a stylet, may be used to advance the helix 46 and the pin electrode 42 to the extended position. As further described above, the helix 46 and the pin electrode 42 may be moved simultaneously. Optionally, the helix 46 and the pin electrode 42 may be rotated to the extended position. As the helix 46 and the pin electrode 42 are rotated, the wires 100 are similarly rotated and un-wound, thus increasing a pitch P between adjacent ones of the wires 100, as compared to the pitch P when the wires 100 are in the retracted state (shown in FIG. 4). In alternative embodiments, rather than rotating, the pin electrode 42 and/or the helix 46 may be forced laterally outward from the housing 60.

In an exemplary embodiment, as illustrated in FIG. 5, the tip 90 of the helix 46 may be substantially aligned with the tip 84 of the pin electrode 42 such that both tips 84 and 90 engage the heart tissue simultaneously. Additionally, when the helix 46 forms part of the shielding member 54, the shielding member 54 covers the entire pacing circuit 50 (shown in FIG. 3). Alternatively, the tip 84 of the pin electrode 42 may extend further than the tip 90 of the helix 46 such that the pin electrode 42 engages the heart tissue prior to the helix 46. The electrode assembly 40 may be stabilized with respect to the heart tissue by the pin electrode 42 prior to, and as, the helix 46 is screwed into, and implanted with, the heart tissue. In such an embodiment, the shielding member 54 almost entirely covers the pacing circuit 50. In other alternative embodiments, the tip 84 of the pin electrode 42 may be recessed with respect to the tip 90 of the helix 46 such that the helix 46 engages the heart tissue prior to the pin electrode 42. In such a situation, the tip electrode 42 would not be embedded as deeply as the helix 46, which would allow for less of the tip electrode 42 interfacing with the heart tissue and would provide entire shielding of the tip electrode 42.

In the extending position, the pin electrode 42 is used to send pacing signals to the tissue of the heart immediately surrounding the portion of the pin electrode 42 that engages the heart tissue. The portion of the pin electrode 42 that engages the heart tissue is referred to as a tissue interface area. The tissue interface area generally extends toward the base 82 from the tip 84. In one exemplary embodiment, the tissue interface area has a surface area of, by way of example only, 4 mm$^2$. The actual surface area may be more or less in alternative embodiments. Optionally, the amount of tissue interface area may be controlled by controlling the amount of extension of the pin electrode 42 from the housing 60. In one embodiment, the amount of extension of the pin electrode 42 may be controlled independently of the amount of extension of the helix 46.

Additionally, because the pin electrode 42 is the only electrically active component of the electrode assembly 40 used for pacing, the total active tissue interface area used for pacing is limited to the tissue interface area of the pin electrode 42. Optionally, the active tissue interface area may be defined as the surface area of the pin electrode 42 that is exposed to the heart tissue at the tissue engaging end 64 of the housing 60, which may include a portion of the tip electrode 42 within the housing 60 due to any tissue ingrowth into the housing 60. While the housing 60 includes a tissue surface area, the portion of the housing 60 that engages the heart tissue would not add to the total active tissue interface area as the housing 60 is electrically inactive. Similarly, while the helix 46 includes a tissue surface area, the portion of the helix 46 that engages the heart tissue would not add to the total active tissue interface area as the helix 46 is electrically inactive.

As illustrated in the Figures, because the pin electrode 42 is straight, the pin electrode 42 has a reduced surface area per depth of insertion into the heart tissue than the helix 46, which is wound around the pin electrode 42. For example, the helix 46 may have approximately three times, or more, the surface area as compared to the pin electrode 42 for a given amount of extension. As such, by providing the pin electrode 42 as the pacing electrode, as opposed to using the helix 46 as a pacing electrode, the active tissue interface area may be greatly reduced. By reducing the active tissue surface area, the impedance of the pacing electrode is increased. By increasing the impedance of the pacing electrode, the battery consumption is reduced during pacing of the heart 16, and the overall battery life may be extended.

In the extended position, the helix 46 is used to permanently affix the lead 12 to the myocardium of the heart 16 (shown in FIG. 1) for a sufficient amount of time to provide cardiac pacing treatment to the heart. For example, the lead 12 may be permanently implanted for the life of the patient, for the life of the battery of the implantable medical device 18, or for another amount of time that the patient may require pacing of the heart 16. Additionally, the helix 46 is used to shield the pacing electrode 42 from electromagnetic fields and/or radiofrequency signals from the MRI system 48.

An MRI-safe implantable lead 12 is thus provided that may be safely used during imaging with the MRI system 48. The lead 12 includes the shielding member 54 that covers the pacing and sensing circuits 50, 52 from electromagnetic fields and/or radiofrequency signals. In an exemplary embodiment, the shielding member 54 includes the shielding conductor 56 (e.g. the wires 100 and the helix 42) The without the generation of significant heat beyond safe temperature levels It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. Dimensions, types of materials, orientations of the various components, and the number and positions of the various components described herein are intended to define parameters of certain embodiments, and are by no means limiting and are merely exemplary embodiments. Many other embodiments and modifications within the spirit and scope of the claims will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112, sixth paragraph, unless and until such claim limitations expressly use the phrase "means for" followed by a statement of function void of further structure.

What is claimed is:

1. An implantable lead comprising:
a lead body, defining a distal end and a proximal end, configured to be implanted in a patient;
an electrode assembly provided at the distal end of the lead body, the electrode assembly comprising an electrode that is configured to deliver stimulating pulses, the electrode extending between a base and a tip at a distal end of the electrode and wherein the electrode assembly further includes an elongated shaft advanceable with respect to the distal end of the lead body, the electrode being coupled to the elongated shaft and being advanceable therewith;
a conductor contained within the lead body and extending from the proximal end of the lead to the base of the electrode assembly; and
a shielding member provided on the electrode assembly the shielding member having a shielding conductor positioned to cover at least a portion of the conductor and the electrode to electrically shield at least a portion of the conductor and a first portion of the electrode from RF fields and a fixation helix for securing the electrode assembly to cardiac tissue of the patient, the fixation helix configured to shield at least a second portion of the electrode from RF fields, wherein the fixation helix and the shielding conductor are electrically isolated from the electrode and wherein the shielding conductor is coupled to the elongated shaft and is advanceable therewith.

2. The implantable lead of claim 1, wherein the shielding conductor wraps about and extends longitudinally along a length of the electrode from the base to the tip.

3. The implantable lead of claim 1, wherein the shielding conductor is helically wound about the electrode.

4. The implantable lead of claim 1, wherein the fixation helix and the shielding conductor are arranged concentrically with one another, and wherein at least one of the fixation helix and the shielding conductor surround at least the tip of the electrode.

5. An implantable lead, comprising:
a lead body, having a distal end and a proximal end, configured to be implanted in a patient;
a stimulating electrode assembly provided at the distal end of the lead body, the stimulating electrode assembly including a housing that holds an electrode therein that is configured to deliver stimulation pulses, the electrode having a conductive body extending between a base and a tip;
a conductor contained within the lead body and extending from the proximal end of the lead to the base of the electrode assembly;
a fixation helix received within the housing for securing the electrode to the cardiac tissue of the patient, the fixation helix wraps about at least a portion of the electrode; and
a shielding conductor electrically coupled to the fixation helix, wherein the shielding conductor electrically shields a portion of the conductor and wherein the shielding conductor and the fixation helix cooperate to electrically shield at least a portion of the electrode from RF fields and wherein the fixation helix and the shielding conductor are electrically isolated from the electrode.

6. The implantable lead of claim 5, wherein the fixation helix includes a tip at a distal end of the fixation helix, the tip of the fixation helix being substantially aligned with the tip of the electrode to shield substantially the entire electrode.

7. The implantable lead of claim 5, wherein the fixation helix extends longitudinally along a length, the electrode being concentrically aligned with the fixation helix.

8. The implantable lead of claim 5, wherein the shielding conductor extends longitudinally along a length within the lead body to a distal end, the distal end being terminated to the fixation helix.

9. The implantable lead of claim 5, further comprising a shaft ring mounted to, and electrically isolated from, the electrode, wherein the helix and the shielding conductor are electrically coupled to one another at the shaft ring.

10. The implantable lead of claim 5, wherein the stimulating electrode assembly further includes an elongated shaft advanceable within the housing, the fixation helix is coupled to the elongated shaft and is advanceable therewith, the shielding conductor is coupled to at least one of the helix and the elongated shaft and is advanceable therewith.

11. The implantable lead of claim 5, wherein the fixation helix includes an insulative coating for electrically isolating the fixation helix from the tissue of the patient.

12. An implantable lead, comprising:
a lead body, having a distal end and a proximal end, configured to be implanted in a patient;
a first pacing conductor extending between the distal end and the proximal end;
an electrode assembly provided at the distal end of the lead body, the electrode assembly including a housing that holds a fixation helix and a distal electrode, the distal electrode being electrically coupled to the pacing conductor and configured to deliver stimulation pulses and wherein the electrode assembly further comprises an elongated shaft movable within the housing;
a proximal electrode proximal of the distal electrode;
a second pacing conductor extending between the proximal end and the proximal electrode; and a shielding member provided within the lead body in electrical isolation from the first and second pacing conductors and surrounding at least a portion of the first and second pacing conductors to electrically shield the pacing conductors from RF fields and wherein the fixation helix and the shielding member are coupled to the elongated shaft and are movable within the housing when the elongated shaft is extended and retracted.

13. The implantable lead of claim 12, wherein the shielding member includes a shielding conductor that extends from the proximal end of the lead body at least to the distal end of the lead body.

14. The implantable lead of claim 12, wherein at least a portion of the shielding member wraps about and extends along the distal electrode.

15. The implantable lead of claim 12, wherein the shielding member includes the fixation helix and a shielding conductor that are arranged concentrically about the distal electrode.

16. The implantable lead of claim 12, wherein a distal end of the distal electrode is substantially flush with a distal end of the fixation helix.

* * * * *